(12) United States Patent
Church

(10) Patent No.: US 11,065,840 B2
(45) Date of Patent: Jul. 20, 2021

(54) STRUCTURES AND METHODS OF MANUFACTURING STRUCTURES USING BIOLOGICAL BASED MATERIALS

(71) Applicant: Ryan Church, Toronto (CA)

(72) Inventor: Ryan Church, Toronto (CA)

(73) Assignee: BIOMERENEWABLES INC., Toronto (CA)

( * ) Notice: Subject to any disclaimer, the term of this patent is extended or adjusted under 35 U.S.C. 154(b) by 205 days.

(21) Appl. No.: 15/553,113

(22) PCT Filed: Feb. 25, 2016

(86) PCT No.: PCT/CA2016/050198
§ 371 (c)(1),
(2) Date: Aug. 23, 2017

(87) PCT Pub. No.: WO2016/134478
PCT Pub. Date: Sep. 1, 2016

(65) Prior Publication Data
US 2018/0037000 A1    Feb. 8, 2018

Related U.S. Application Data

(60) Provisional application No. 62/120,409, filed on Feb. 25, 2015.

(51) Int. Cl.
*B32B 9/02* (2006.01)
*F03D 13/10* (2016.01)
(Continued)

(52) U.S. Cl.
CPC ............... *B32B 9/02* (2013.01); *B64C 3/00* (2013.01); *C12N 1/16* (2013.01); *C12N 9/80* (2013.01);
(Continued)

(58) Field of Classification Search
CPC .. C12N 1/16; C12N 9/80; C12N 11/00; F01D 5/147; F01D 21/003; F03D 13/10;
(Continued)

(56) References Cited

U.S. PATENT DOCUMENTS

2010/0055438 A1*  3/2010  Kaplan ................. A61L 27/227
                                                          428/221
2011/0027850 A1   2/2011  Crawford et al.
(Continued)

FOREIGN PATENT DOCUMENTS

CA         2591097        6/2006
CN       103029395 A      4/2013
(Continued)

OTHER PUBLICATIONS

Krampitz et al, "Molecular Mechanisms of Biomineralization in the Formation of Calcified Shells," 1988, Angew. Chem. Int., vol. 27, pp. 1145-1156 (Year: 1988).*
(Continued)

*Primary Examiner* — Maria V Ewald
*Assistant Examiner* — Ethan Weydemeyer
(74) *Attorney, Agent, or Firm* — Norton Rose Fulbright Canada LLP

(57) ABSTRACT

A structure for a turbine, the structure comprising a body having a multi-layer construction including an interior layer with substantially uniform concentrations throughout of facultative anaerobic organisms (FAO) that have gene sets capable of producing the enzyme urease and/or the proteins purloin, lustre A and perlustrin, along with glucose, and non-uniform concentrations throughout of a structural composition, the structural composition including a chitin-based component with silk fibronectin and water; an exterior layer of urea, water, calcium ions and facultative anaerobic organisms (FAOs) including urease, aragonite; and a binding layer
(Continued)

of conchiolin protein intermediate the interior layer and the exterior layer. The facultative anaeorobic organisms (FAOs) are organisms classified in one of the *Saccharomyces, Escherichia* and *Bacillus* genuses.

17 Claims, 7 Drawing Sheets

(51) Int. Cl.
| | |
|---|---|
| F03D 1/06 | (2006.01) |
| C12N 9/80 | (2006.01) |
| C12N 1/16 | (2006.01) |
| C12N 11/00 | (2006.01) |
| B64C 3/00 | (2006.01) |
| F01D 5/14 | (2006.01) |
| F01D 21/00 | (2006.01) |
| B64C 3/46 | (2006.01) |
| B64C 3/30 | (2006.01) |
| B64D 15/16 | (2006.01) |
| F03D 80/40 | (2016.01) |
| B33Y 70/00 | (2020.01) |
| B33Y 10/00 | (2015.01) |
| C12P 1/00 | (2006.01) |

(52) U.S. Cl.
CPC ............... *C12N 11/00* (2013.01); *F01D 5/147* (2013.01); *F01D 21/003* (2013.01); *F03D 1/065* (2013.01); *F03D 1/0675* (2013.01); *F03D 13/10* (2016.05); *B33Y 10/00* (2014.12); *B33Y 70/00* (2014.12); *B64C 3/30* (2013.01); *B64C 3/46* (2013.01); *B64D 15/166* (2013.01); *C12P 1/00* (2013.01); *F03D 1/0641* (2013.01); *F03D 1/0683* (2013.01); *F03D 80/40* (2016.05); *F05B 2230/30* (2013.01); *F05B 2230/50* (2013.01); *F05B 2230/80* (2013.01); *F05B 2240/21* (2013.01); *F05B 2240/57* (2013.01); *F05B 2270/107* (2013.01); *F05B 2270/17* (2013.01); *F05B 2270/301* (2013.01); *Y02B 10/30* (2013.01); *Y02E 10/72* (2013.01); *Y02P 70/50* (2015.11)

(58) Field of Classification Search
CPC ......... F03D 1/065; F03D 1/0675; B32B 9/02; F05B 2230/30; F05B 2230/50; F05B 2230/80; F05B 2240/21; F05B 2240/57; F05B 2270/107; F05B 2270/17; F05B 220/301; Y02B 10/30; Y02B 10/72; B33Y 10/00; B33Y 70/00
See application file for complete search history.

(56) References Cited

U.S. PATENT DOCUMENTS

| | | |
|---|---|---|
| 2011/0079936 A1 | 4/2011 | Oxman |
| 2011/0262640 A1 | 10/2011 | Dosier |
| 2014/0248681 A1* | 9/2014 | Soens ................ C04B 20/1029 435/182 |
| 2015/0158244 A1 | 6/2015 | Tibbets et al. |
| 2016/0107287 A1* | 4/2016 | Bajaj ..................... B24B 37/22 51/298 |

FOREIGN PATENT DOCUMENTS

| | | | |
|---|---|---|---|
| CN | 203680807 U | 7/2014 | |
| CN | 105 019 950 | 11/2015 | |
| EP | 2082999 | 7/2009 | |
| JP | S6325031 A | 2/1988 | |
| WO | WO-2010056098 A1 * | 5/2010 | ............ C04B 24/14 |

OTHER PUBLICATIONS

Subhapradha et al, "Phys. Char. of B-Chitosan from Sepioteuthis lessoniana gladius," Apr. 15, 2013, Elsevier (Food Chemistry), Issue 141, pp. 907-913 (Year: 2013).*
Supplementary European Search Report and Written Opinion issued in European Application No. PCT/CA2016/050198, dated Aug. 14, 2018.
Liu et al., "Fabricating Three-Dimensional Carbohydrate Hydrogel Microarray for Lectin-Mediated Bacterium Capturing", Biosensors and Bioelectronics, vol. 58, p. 92-100, Aug. 1, 2014.
Marin et al., "The Formation and Mineralization of Mollusk Shell", Frontiers in Bioscience S4, p. 1099-1125, Jan. 1, 2012.
Nakamura et al., "Biomatrices and Biomaterials for Future Developments of Bioprinting and Biofabrication", Biofabrication, vol. 2, No. 1, p. 014110, Mar. 1, 2010.
Billiet et al., "Development of Optimized Autonomous Self-Healing Systems for Epoxy Materials Based on Maleimide Chemistry", Polymer, Elsevier Science Publishers B.V., GB, vol. 53, No. 12, p. 2320-2326, Mar. 29, 2012.
Church et al., "Putting the Nosecone to Work: Innovations in the Design of a Power-Producing Spinner", EWEA Annual Conference Hamburg 2016, p. 1-3, Jan. 1, 2016. https://windeurope.org/summit2016/conference/submit-an-abstract/pdf/664885160596.pdf.
Pescovitz et al., "Introduction: Nature as Source and Code", p. 1-20, Dec. 1, 2006. http://www.iftf.org/uploads/media/SR-1051_Intentional_Biology.pdf.
Luca et al., "A Novel Bioluminescent NanoLuc Yeast-Estrogen Screen Biosensor (nanoYES) With a Compact Wireless Camera for Effect-Based Detection of Endocrine-Disrupting Chemicals", Analytical and Bioanalytical Chemistry, Springer, DE, vol. 410, No. 4, p. 1237-1246, Sep. 30, 2017.
Kyle et al., "3D Printing of Bacteria: The Next Frontier in Biofabrication", Trends in Biotechnology, vol. 36, No. 4, p. 340-341, Apr. 1, 2018.
Matt et al., "Self-Healing of Wind Turbine Blades Using Microscale Vascular Vessels", Journal of Energy Resources Technology, vol. 139, No. 5, Mar. 16, 2017.
First Chinese Office Action issued in Chinese Application No. 201680018074.5, dated Jan. 9, 2019.
EPO, Office Action for European Patent Application No. 16 754 710.8 dated Jul. 17, 2020.

* cited by examiner

STRUCTURES AND METHODS OF MANUFACTURING STRUCTURES USING BIOLOGICAL BASED MATERIALS

CROSS-REFERENCE TO RELATED APPLICATION

This application claims priority under 35 U.S.C. 119(e) from U.S. Provisional Patent Application Ser. No. 62/120, 409 entitled "METHOD OF MANUFACTURING AND MAINTAINING WIND TURBINE COMPONENTS" filed on Feb. 25, 2015, the contents of which are incorporated in their entirety herein by reference.

FIELD OF THE INVENTION

The following relates generally to manufacturing of structures, and more particularly to additive manufacturing of structures using biological-based materials.

BACKGROUND OF THE INVENTION

Horizontal-axis wind turbines for generating electricity from rotational motion are generally comprised of one or more rotor blades each having an aerodynamic body extending outwards from a horizontal shaft or hub that is supported by, and rotates within, a wind turbine nacelle. The nacelle is supported on a tower which extends from the ground or other surface. The hub is also covered by a nose cone, spinner or fairing. Wind incident on the rotor blades applies pressure causing the rotor blades to move by rotating the shaft from which they extend about the horizontal rotational axis of the shaft. The shaft is, in turn, associated with an electricity generator which, as is well-known, converts the rotational motion of the shaft into electrical current for transmission, storage and/or immediate use. Horizontal-axis wind turbines are generally very well-known and understood, though improvements in their operation to improve the efficiency of power conversion and their overall operational characteristics are desirable.

The rotor blades, hub, spinner, nosecone, and nacelle are all separate parts that are manufactured at a manufacturing facility and then transported to the wind farm location for assembly. The transportation of these separate parts incurs significant costs for the operators and manufacturers, and thus, there may be a more effective and cost-efficient way to manufacture a wind turbine at the site of electricity production.

There are several ways to manufacture wind turbine components, including rotor blades, hubs, spinners, nosecones, and nacelles that are used across the industry. These include, but are not limited to, hand layup, filament winding, prepreg, pultrusion, vacuum-infusion and resin transfer moulding of various synthetic fibres, thermoplastic composites and laminates. All of these processes and materials are presently used to create rotor blades and other wind turbine components that contain bonded joints, shear webs and spar caps, among others. These processes involve labour-intensive and costly methods, and thus, there may be a way to improve the time and cost of manufacturing these components.

Rotor blades in particular are currently manufactured using a shell-sandwich technique or modular techniques that produce areas of failure in wind turbines. These failures include but are not limited to, buckling, fibre failure, inter-fibre failure, bond failure and/or erosion of bonded joins, spar caps, trailing edges, leading edges, trailing edge spars, leading edge spars and/or shear webs. These modes of failure represent a significant cost to wind turbine manufacturers and wind farm operators, while also being a safety concern and leading to a loss of energy production and efficiency.

Biomimetics is the imitation of nature when addressing complex engineering and design problems, and has gained attention in the field of renewable energy production. However, the application of biomimetics to specific problems in the field of wind turbine manufacturing, such as those involving organic material usage, deposition patterns and materials gradients is still nascent. Attempts to solve complex manufacturing problems using biomimetics without careful consideration have often failed to take into account certain key characteristics such as scale, material suitability, and form to functional fit.

Synthetic biology is the manipulation of gene sets and genomic material within the cell for useful purposes, and has gained attention within the field of biological manufacturing. However, the application of synthetic biology to specific problems in the manufacturing and maintenance of large structures, such as wind turbine components, is still nascent.

Additive manufacturing, known commonly as 3D printing is, a robust method of making objects through successive layers of material deposition from computer generated CAD models and has gained attention within the field of manufacturing. However, the application of additive manufacturing to specific problems in the manufacturing of wind turbine components has remained at the creation of mould structures for components to be further manufactured via traditional methods outlined above, as in Chinese Patent No. CN203680807U.

More specifically, the manufacturing of these mould structures has been limited to non-biological materials. The field of biological additive manufacturing through the use of biologically-based feed stocks has emerged in some industries as a valuable was to create sustainable and environmentally conscious products. However, the application of biological additive manufacturing to specific problems in the manufacturing and maintenance of large engineered structures, such as wind turbine components, is still nascent.

Various manufacturing techniques are of interest. For example United States Patent Application Publication No. 2015/0158244 to Skyler Tibbits et al. entitled "OBJECT OF ADDITIVE MANUFACTURE WITH ENCODED PREDICTED SHAPE CHANGE AND METHOD OF MANUFACTURING SAME" discloses an object comprising an additive manufacturing material, the additive manufacturing material having a response to an external stimulus and being configured to cause a predicted transformation of the object from a first manufactured shape to a second manufactured shape in response to the external stimulus, the external stimulus being non-biasing with respect to the predicted transformation from the first manufactured shape to the second manufactured shape.

European Patent Application Publication No. EP 2,082, 999 to Jonkers entitled "HEALING AGENT IN CEMENT-BASED MATERIALS AND STRUCTURES, AND PROCESS FOR ITS PREPARATION" discloses a healing agent in cement-based materials and structures, characterized in that said healing agent comprises organic compounds and/or bacteria-loaded porous particles.

United States Patent Publication No. 2011/0079936 to Neri Oxman entitled "METHODS AND APPARATUS FOR VARIABLE PROPERTY RAPID PROTOTYPING" discloses an apparatus for fused deposition, comprising at least one nozzle for extruding material and at least one actuator for moving said nozzle, the improvement comprising at least one chamber adapted for mixing a plurality of materials for extrusion though said nozzle, in such a manner that the ratio of said materials in said extruded mixture varies in a substantially continuous gradient.

SUMMARY OF THE INVENTION

According to an aspect, there is provided a structure for a turbine, the structure comprising a body having a multi-layer construction including: an interior layer with substantially uniform concentrations throughout of facultative anaerobic organisms (FAOs) that have gene sets capable of producing the enzyme urease and/or the proteins purloin, lustre A and perlustrin, along with glucose, and non-uniform concentrations throughout of a structural composition, the structural composition including a chitin-based component with silk fibronectin and water; an exterior layer of urea, water, calcium ions and facultative anaerobic organisms (FAOs) including urease, aragonite; and a binding layer of conchiolin protein intermediate the interior layer and the exterior layer.

According to another aspect, there is provided a structure produced by additive manufacturing using multiple layers at least one of which includes varying concentrations of both organic and inorganic substances in non-uniform concentrations thereby to provide non-uniform structural properties. The structure may be a rotor blade, According to another aspect, there is provided a method of multi-material additive manufacturing of the structures, where the final structure is printed on-site and/or in situ, the method comprising instructing an additive manufacturing machine with at least one extruder nozzle, at least one actuator motor and an ability to navigate around the entire base and height of the desired structure, the additive manufacturing machine being in fluid communication with a material feedstock(s) to add successive layers of various material to a base, by a processing structure configured using processor-readable program code stored on a processor-readable medium containing data for the overall shape of the structure and the various material concentrations, spacings and gradients.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures wherein.

DETAILED DESCRIPTION

Reference will now be made in detail to the various embodiments of the invention, one or more examples of which are illustrated in the figures. Each example is provided by way of explanation of the invention, and is not meant as a limitation of the invention. For example, features illustrated or described as part of one embodiment can be used on or in conjunction with other embodiments to yield yet a further embodiment. It is intended that the present invention includes such modifications and variations.

The following includes description of opportunities for improving on the traditional aspects of manufacturing structures such as wind turbine components and to provide adaptations to the materials used and the location of their manufacture in order to improve upon the integrity, longevity, and cost-efficiency of the components and accordingly to the wind turbine as a whole. In particular, improvements based on additive manufacturing in various locations using a plurality of biological and non-biological materials as appropriate in various gradients in tandem with synthetically-modified single-cell organisms for material production and incorporation into manufactured components as appropriate through biomimetic models of scaffolds, matrices and meshes to the rotor blades, hubs, spinners/nose cones, and/or nacelles of a wind turbine are provided.

Figure 1:
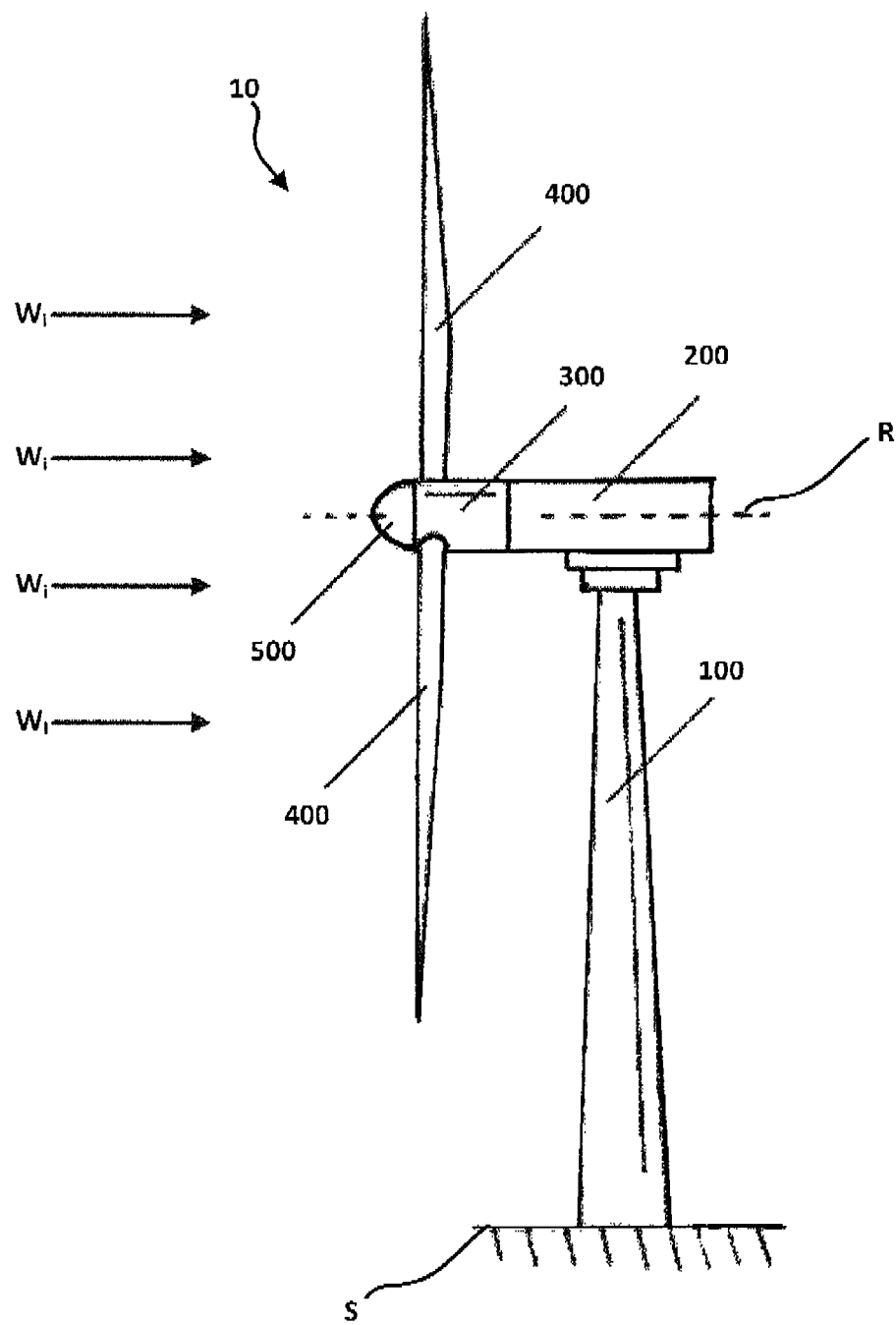
FIG. 1 is a side elevation view of a horizontal axis wind turbine, according to the prior art.

FIG. 1 is a side elevation view of a horizontal axis wind turbine 10, according to the prior art. Wind turbine 10 includes a tower 100 supported by and extending from a surface S, such as a ground surface. Supported by tower 100, in turn, is a nacelle 200 extending horizontally. A hub with a spinner 300 is rotatably mounted at a front end of nacelle 200 and is rotatable with respect to nacelle 200 about a rotation axis R. Spinner 300 receives and supports multiple rotor blades 400 that each extend outwardly from spinner 300. Rotor blades 400 catch incident wind W, flowing towards the wind turbine 10 and are caused to rotate. Due to their being supported by spinner 300, rotor blades 400 when rotating cause spinner 300 to rotate about rotation axis R thereby to cause rotational motion that can be converted in a well-known manner into usable electrical or mechanical power. In this sense, rotor blades 400 are each structures adapted to traverse a fluid environment, where the fluid in this embodiment is ambient air. Nacelle 200 may be rotatably mounted to tower 100 such that nacelle 200 can rotate about a substantially vertical axis (not shown) with respect to tower 100, thereby to enable rotor blades 400 to adaptively face the direction from which incident wind W, is approaching wind turbine 10. A nose cone 500 of generally a uniform paraboloidal shape is shown mounted to a front end of spinner 300 to deflect incident wind W, away from spinner 300.

Figure 2:
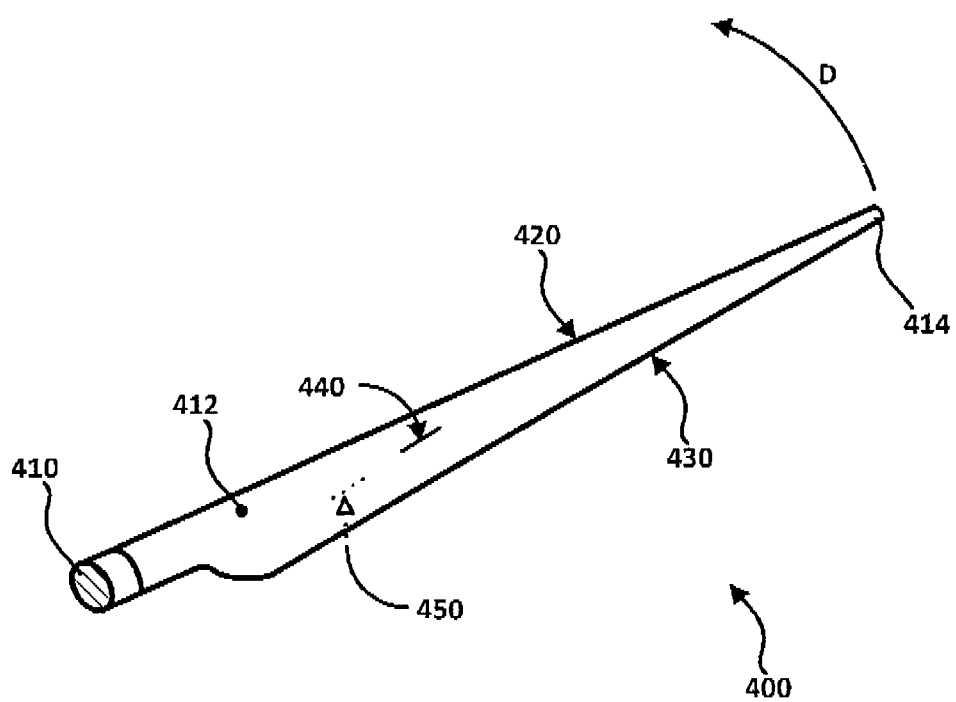
FIG. 2 is a front perspective view of a rotor blades for the turbine of FIG. 1, in isolation, according to the prior art.

FIG. 2 is a front perspective view of one of rotor blades 400 in isolation. Rotor blade 400 includes an elongate body that extends from a root 410 through a main section 412 to terminate at a wingtip 414. Root 410 extends from nacelle 200 when attached thereto or integrated therewith, whereas wingtip 414 is the portion of the elongate body that is distal to nacelle 200. The elongate body has a leading edge 420 and a trailing edge 430, where leading edge 420 leads trailing edge 430 when rotor blade 400 is in motion rotating with nacelle 200 about rotation axis R in the direction D. A suction side 440 of the elongate body is shown in FIG. 2, and a pressure side 450, shown in dotted lines, is opposite the elongate body from suction side 440.

Figure 3:
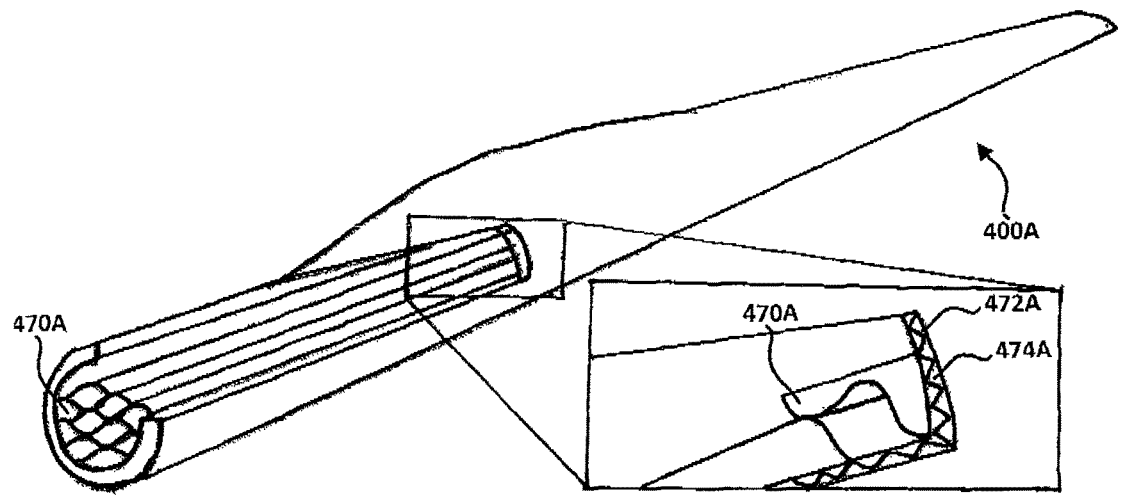
FIG. 3 is an end perspective cross-sectional view of a rotor blade for a horizontal-axis wind turbine with an enlarged view of the internal structures, including a plurality of varying scaffolds, matrices and/or meshes, according to an embodiment of the invention.

FIG. 3 is an end perspective cross-sectional view of a rotor blade 400A for a horizontal-axis wind turbine with an enlarged view of the internal structures, including a plurality of varying scaffolds, matrices and/or meshes 470A, according to an embodiment of the invention. In this embodiment, the rotor blade 400A has an outer skin 472A that has a high concentration of mineral-fibres and chitin, in a lattice network 474A with hollow spaces. This network is created through successive layers of material deposition at varying concentrations throughout the matrix. Turning again to the enlarged view, there appears a wave pattern mesh 470A connected at points along its length with various degrees of flexibility through the vertical layers of material, with the most rigid material at the connection point, and the most flexible property midway between these two connection lengths. The negative space of this enlarged view represents a hollow tunnel that may be filled with a gas other than air that is beneficial to the growth of a single-celled organism.

Figure 4:
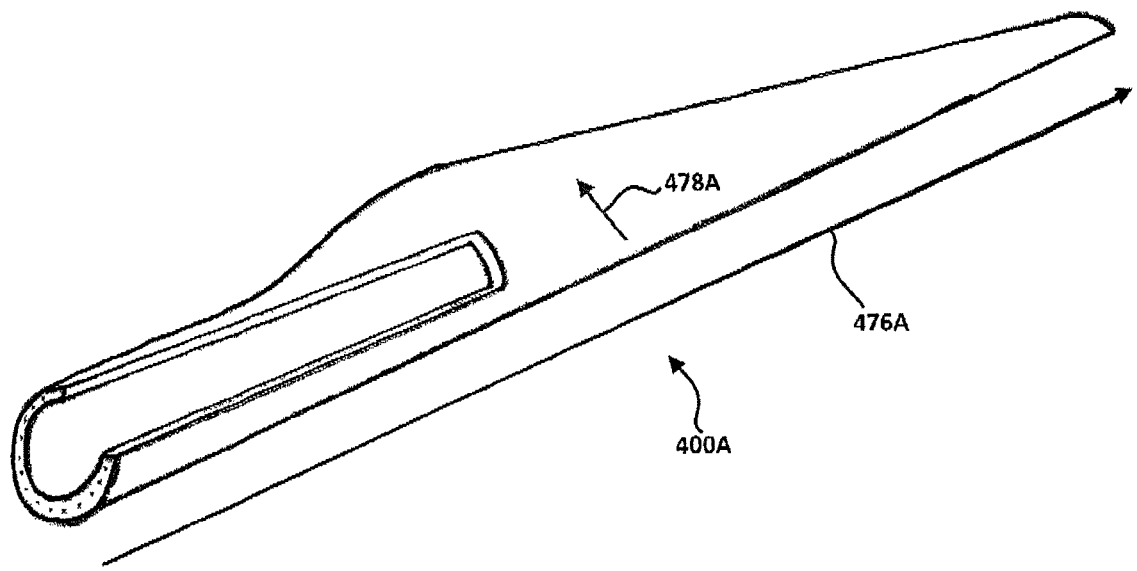
FIG. 4 is an end perspective view of the rotor blade of FIG. 3 showing material gradients both along and across the rotor blade, according to an embodiment of the invention.

FIG. 4 is an end perspective view of the rotor blade 400A of FIG. 3 showing material gradients both along and across the rotor blade, according to an embodiment of the invention. An arrow 476A along the length of the rotor blade 400A and an arrow 478A along the width which describes the decrease in material density and concentration. This decrease relates to the stiffness of the material chosen, the concentration of the fibre to mineral concentration and gradient or concentration of its deployment as a whole. Further to this, there may be an increase in the chamber volume along these lengths, with less material towards the arrow head.

Figure 5:
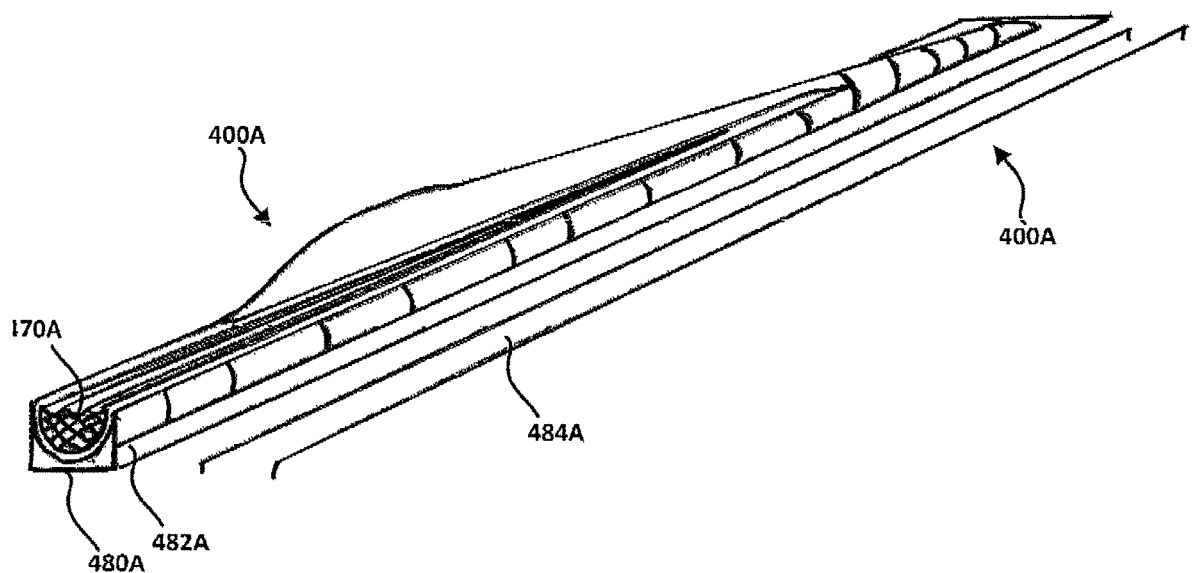
FIG. 5 is an end perspective view of the rotor blade of FIG. 3 prior to being completely produced through additive manufacturing, according to an embodiment of the invention.

FIG. 5 is an end perspective view of the rotor blade 400A of FIG. 3 prior to being completely produced through additive manufacturing, according to an embodiment of the invention. A base or support 480A for material deposition can be seen, along with an example of the inner matrix 470A, and the support scaffold 482A, the instructions for the deposition of which is incorporated into a CAD model that includes instructions for the additive manufacturing of rotor blade 400A, depending on the weight and proportions of the object to be printed. The scaffold 482A is intended to be removed after manufacturing of the component through physical force, grinding and/or sanding as is described in United States Patent Application Publication No. 2013/0295338 to Keating and Oxman entitled "METHOD AND APPARATUS FOR COMPUTER-ASSISTEND SPRAY FOAM FABIRCATION".

Also shown in FIG. 5 is a track 484A for guiding an additive manufacturing device (not shown in FIG. 5) along parallel lines and along the length of the structure being produced. This effect may be similar replicated in the production of objects longer than the reach of the additive manufacturing device's arm, using wheels under control of a processing structure (not shown in FIG. 5), or a similar structure that enables the additive manufacturing device to translate along the track 484A.

Figure 6:
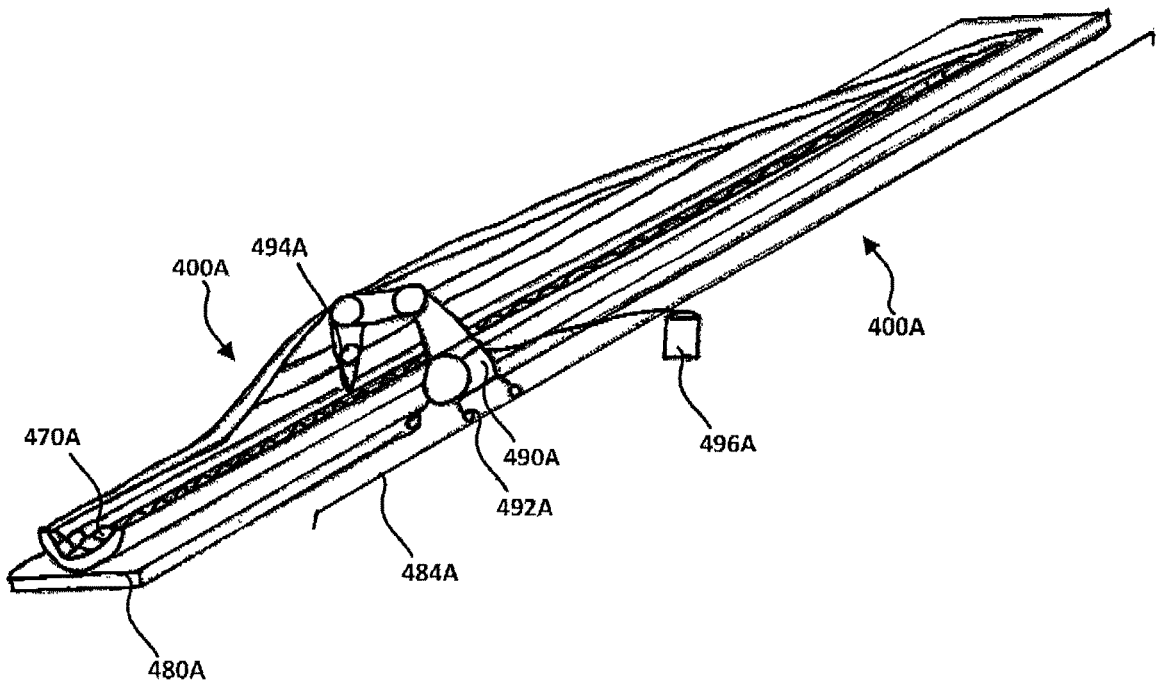
FIG. 6 is an end perspective view of the rotor blade of FIG. 3 prior to being completely produced through additive manufacturing, and components for additive manufacturing of the rotor blade, according to embodiments of the invention.

FIG. 6 is an end perspective view of the rotor blade 400A of FIG. 3 prior to being completely produced through additive manufacturing, and components for additive manufacturing of the rotor blade 400A, according to embodiments of the invention. An additive manufacturing device 490A is guided along track 484A through wheels 492A, while an extruder head 494A expels a plurality of biological and non-biological materials in varying concentrations and gradients through a material holding tank 496A onto base 480A.

Figure 7:
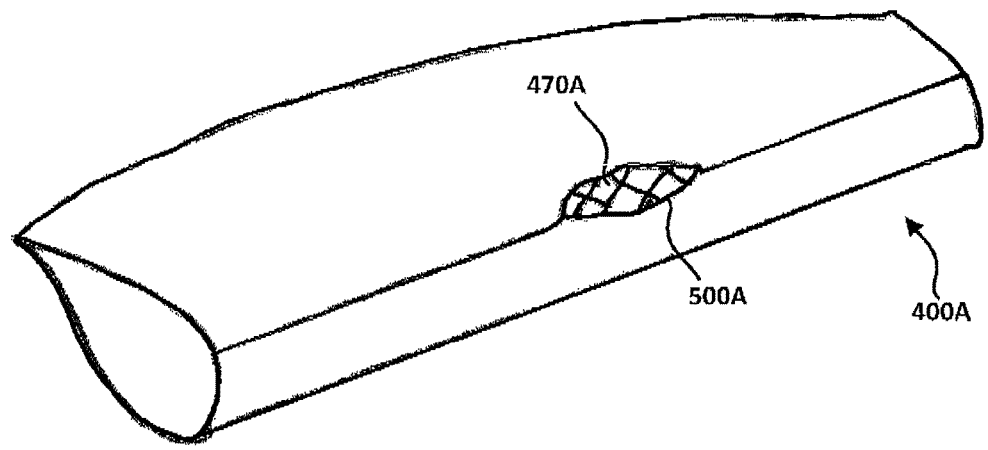
FIG. 7 is an enlarged front leading edge view of a portion of rotor blade of FIG. 3 having a damaged portion.

FIG. 7 is an enlarged front leading edge view of a portion of rotor blade 400A of FIG. 3 having a damaged portion 500A. The damaged portion 500A reveals the inner matrix 470A, which would then equilibrate to the ambient environmental conditions, causing a change in metabolic conditions of any single-celled organisms that were being hosted within the structure as will be described.

Figure 8:
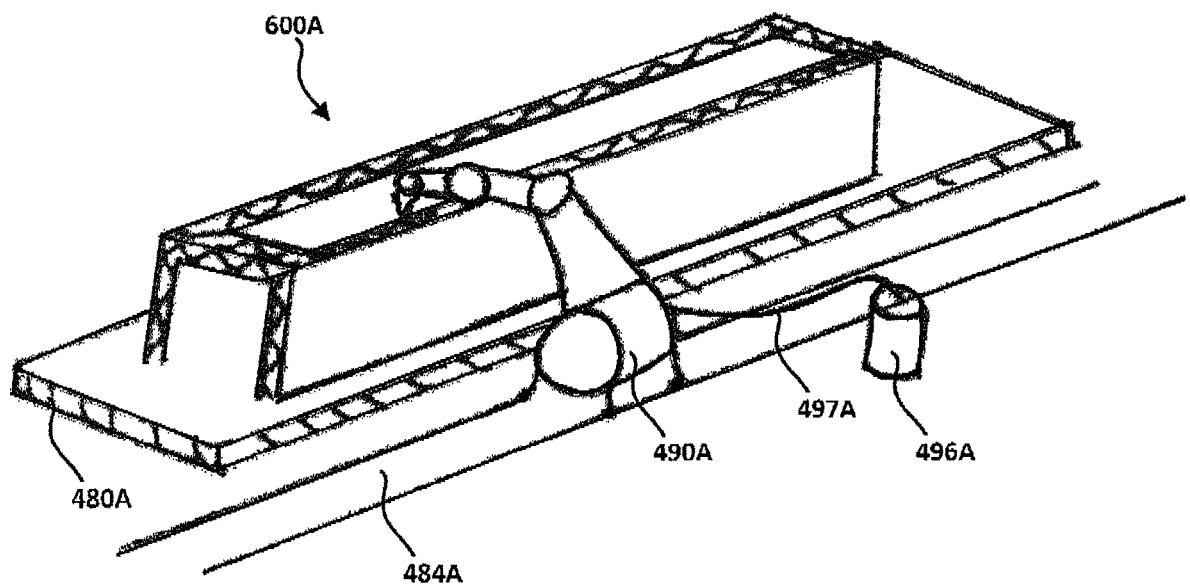
FIG. 8 is an end perspective view of a nacelle for a horizontal-axis wind turbine prior to being completely produced through additive manufacturing, and components for additive manufacturing of the nacelle, according to an embodiment of the invention.

FIG. 8 is an end perspective view of a nacelle 600A for a horizontal-axis wind turbine prior to being completely produced through additive manufacturing, and components for additive manufacturing of the nacelle 600A, according to an embodiment of the invention. The additive manufacturing device 490A is guided along tracks 484A and remains in fluid communication with material holding tank 496A via a feeder tube 497A for depositing material onto base 480A in successive layers, building up the structure.

Figure 9:
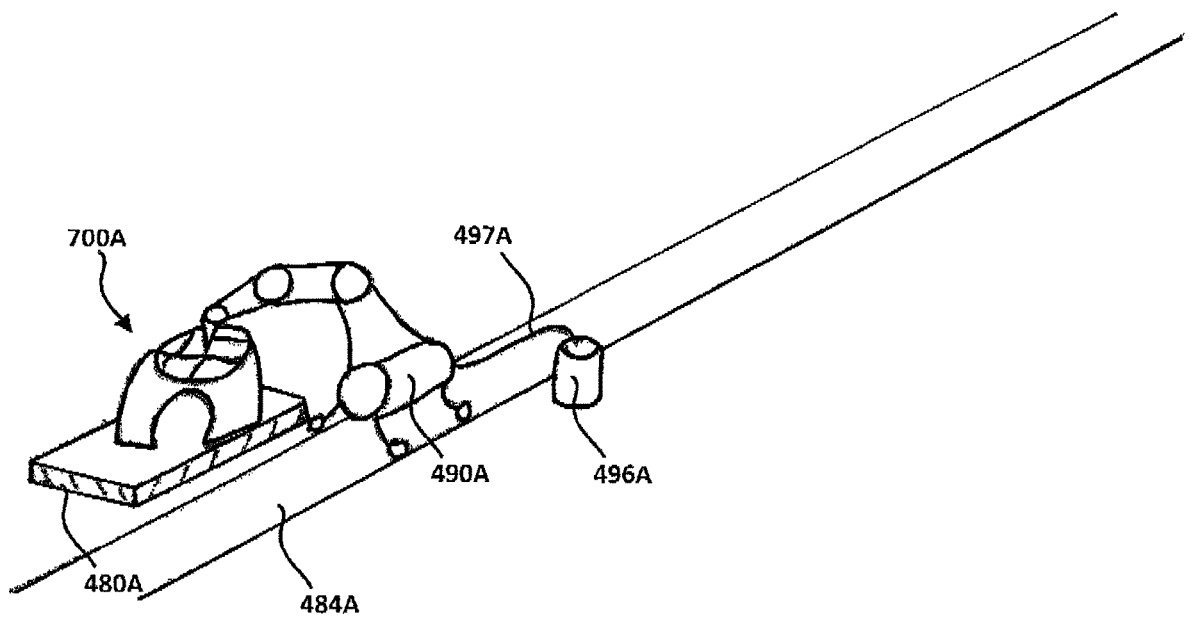
FIG. 9 is a perspective view of a spinner for a horizontal-axis wind turbine prior to being completely produced through additive manufacturing, and components for additive manufacturing of the spinner, according to embodiments of the invention.

FIG. 9 is a perspective view of a spinner 700A for a horizontal-axis wind turbine prior to being completely produced through additive manufacturing, and components for additive manufacturing of the spinner 700A, according to embodiments of the invention. The additive manufacturing device 490A is guided along tracks 484A and remains in fluid communication with material holding tank 496A via a feeder tube 497A for depositing material onto base 480A in successive layers, building up the structure.

Figure 10:
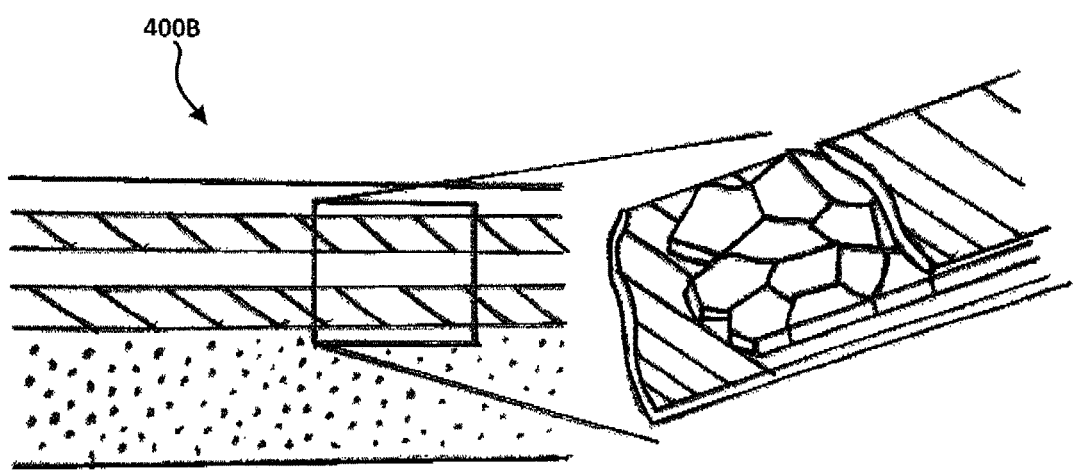
FIG. 10 is a side cross-sectional view of a portion of a rotor blade, according to an alternative embodiment.
Figure 11:
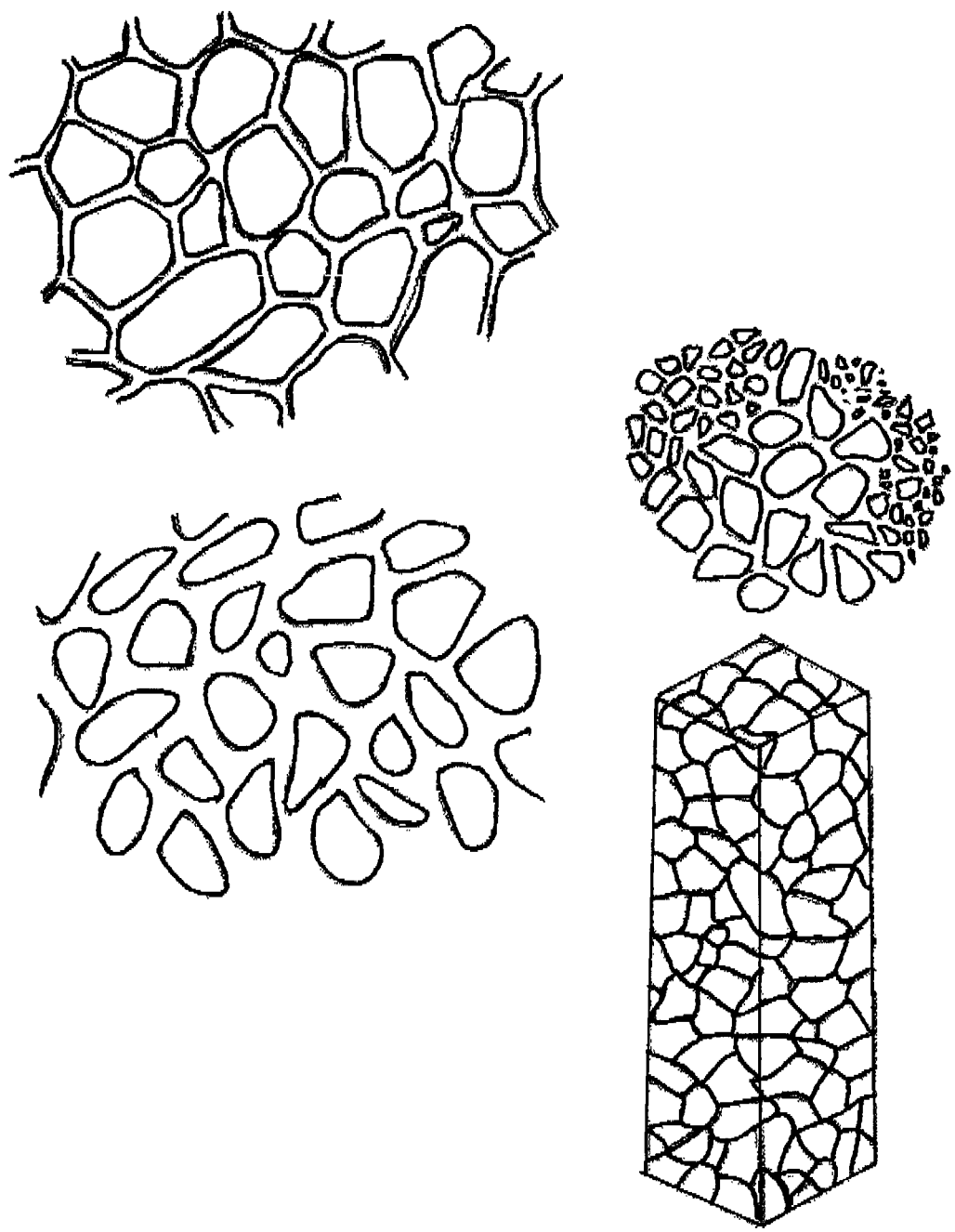
FIG. 11 shows various voronoi patterns.

FIG. 10 is a side cross-sectional view of a portion of a rotor blade 400B, according to an alternative embodiment, including portions of material deposited in Voronoi patterns for scaffolds, matrices and meshes. FIG. 11 shows various voronoi patterns.

The above-described improvements to the manufacturing procedure of horizontal-axis wind turbine components can also be applied to vertical-axis wind turbines, and may apply equally well, mutatis mutandis, with such mutations as being relevant, including but not limited to, large engineered objects greater than 1 centimetre cubed, including: airplane wings, airfoils, helicopter blades, aerospace rockets, the hulls of ships, bridges, buildings, automobiles and other things. The invention or inventions described herein may be applied to wind turbines having fewer or more blades than described by way of example in order to increase the operational efficiency of a wind turbine, to decrease noise emissions, to decrease maintenance costs, and to increase the scalability and marketability of such wind turbines.

In regards to the materials being deposited, multi-material additive manufacturing principles are described which mimic arthropod and mollusk shell development through the deposition of precursor building blocks which self-assemble over time (4D printing) through the precise hierarchical arrangement of organic (protein) and inorganic (mineral) deposition, forming a material matrix with different structural properties than the precursor deposition. This matrix further contains impregnated facultative anaerobic organisms (FAOs) to mimic the cellular machinery of arthropods and mollusks in gene set availability and protein secretion where damage occurs. The composition and content of varying facultative anaerobic organisms is related to their environment, and the desired material matrix. Environmental triggers signal the activation of gene sets, production of proteins and realization of building blocks within the matrix, which self-assemble due to cascading energy gradients. Alternating layers of material, varying by composition, concentration and pH, along with their associative FAOs to give structural conformity. Techniques in synthetic biology, such as CRISPR, are used to produce the constructs of the FAI for each material type and variation in concentrations and gradients therein.

According to these principles, the 3D additive manufacturing equipment may be thought of as the organism for initial production. After printing is complete, the imbedded FAOs represent the gene analogues of the cellular machinery within the model organism. Being printed therefore is somewhat of an engineered living organism that is capable of responding to cues from its environment, but whose role is for reinforcing structure rather than modifying actual structure shape in response to such environment cues.

A model organism, and thus the gene sets and protein production required, is context and content specific to the material used, its function and environment, where that be on land, air, sea or in space. Various organic and inorganic building blocks are known on earth, while other inorganic building blocks are known in space. Organic building blocks found in space are yet to be described. A knowledge of nature's recipe and technique for building structures in certain environments can play a crucial role in the material selected for certain applications.

For example, the thruster of a ship may be manufactured out of aragonite, a form of calcium carbonate ($CaCO_3$), using a method inspired by the organic/inorganic recipe that a mollusk uses to build its shell. This resulting engineered bio-ceramic would confer a number of the same properties found in the shell of a mollusk. Through the deposition of proteins and urea, calcium ions precipitate out of sea water, self-assembling into Beta-pleated sheets on the growing face of the crystal. Another protein may then be secreted to stop this mineralization, halting growing. As such, a ship thruster manufactured out of aragonite, and impregnated with FAOs analogous to the gene sets of mollusk epithelial tissue could thus generate the required protein scaffold to facilitate self-assembly of new aragonite in a damaged region of the thruster, given the correct environmental cue. Given an alternate cue, self-assemble could also terminate.

FAOs may be any suitable bacterial or eukaryotic model organism. Beneficially, these organisms are able to switch metabolic pathways given environmental conditions. They make ATP by aerobic respiration if oxygen is present, but are able to switch to fermentation or anaerobic respiration if oxygen is absent. Thus, these organisms are able to survive on land, air, sea and even space.

Organisms from the Genus *Saccharomyces, Escherichia* and/or *Bacillus* are particularly useful as all are facultatively anaerobic. *Saccharomyces cerevisiae* is known to naturally contain chitin synthase, *Escherichia coli* has been well studied, and *Bacillus* induces 'microbiologically induced calcium carbonate precipitation' (MICP).

Organic building blocks may include polysaccharides such as chitin, chitosan, cellulose, keratin, which all have glucose as their monomer. Silk fibroins are a type of keratin, and contain the form of a Beta-pletted sheet. Chitin, cellulose, keratin also come as Beta-pleated sheets, thus enabling the structural conformity mentioned above.

Other building blocks include proteins, which vary widely depending on the tissue type of the organism being modelled and the material to be printed.

Inorganic building blocks include calcium carbonate, calcium phosphate, Goethite, and the like.

In the present context, combining organic and inorganic materials can provide unique and beneficial structural properties.

By way of example, a wind turbine blade additively manufactured by this novel method is given. In this embodiment, there are three (3) distinct layers. An inner-most layer includes a beta-chitin, beta-chitosan, silk fibronectin and water, whose concentration varies, along with glucose and FAOs, whose concentration does not vary. In this case, the FAO could be *S. cerevisiae*, whose CHS chitin synthase gene-set turns glucose into self-assembling nano-fibrils of N-acetylglucosamine, forming beta-chitin, much like arthropods upon environmental stimulus. The varying concentrations of beta-chitosan, silk fibronectin and water give varying structural properties, which can be adjusted as desired by computational analysis.

An alternative composition includes an inner-most layer comprising N-acetylglucosamine (GlcNAc)—the monomeric form of beta-chitin, silk fibronectin and water, whose concentration varies, along with glucose and FAOs, whose concentration does not vary. The FAOs could be *S. cerevisiae*, whose CHS chitin synthase gene-set facilitates the polymerization of GlcNAc into nano-fibrils of beta-chitin. The FAOs can also act in a self-healing matter upon environmental stimulus. The varying concentrations of GlcNAc, silk fibronectin and water give varying structural properties, which can be adjusted as desired by computational analysis.

The printing speed between successive passes in determined by the polymerization speed and the self-assembly of the varying elements.

An outer-most matrix layer may comprises precursor products urea, water, calcium ions and FAOs. FAOs with microbial Urease produces calcium carbonate from the precursor products, which takes the form of aragonite through contact with the protein conchiolin (a protein/chitin polymer produced from the FAOs) and takes the structural form of beta-pleated sheets through the amino acids MSI60, MSI31, forming ridged and crack-resistant layers of aragonite between alternating conchiolin layers. Other proteins encoded for in the FAO include purloin, lustre A and perlustrin.

An intermediate binding layer may comprises chitin and/or aragonite composed of conchiolin protein.

Structural conformity is seen as all material types are Beta-pleated sheets.

The outmost layer of aragonite, also known as nacre, is corrosion resistant to rain and air particulate that effect modern wind turbine rotor blades. The inner structure is lighter than aragonite, and its properties allow varying stiffness gradients to be applied, thus allowing the tip of a rotor blade, for example, to be flexible, while the root can be firm.

In embodiments disclosed, the multi-material 3D printing may be done where, or near to where, the final structure (rotor blade, nacelle, spinner or other component for a wind turbine or other structure for use in another context) is printed on-site and/or in situ. A the method comprising having a computer-readable file on a computer containing specifications about the overall shape of the structure to be produced in addition to the various material concentrations, spacings and gradients along the structure, a flat base assembled from plywood or the like, a material printer with at least one extruder nozzle, at least one actuator motor and an ability to navigate around the entire base and height of the desired object and connected to the material feedstock(s).

Although embodiments have been described with reference to the drawings, those of skill in the art will appreciate that variations and modifications may be made without departing from the spirit and scope thereof as defined by the appended claims.

The above-described rotor blade configurations for a horizontal-axis wind turbine can also be applied to one or more rotor blades usable for vertical-axis wind turbines, and both of any scale, or to one or more rotor blades usable in hydroelectric dam turbines, gas turbines, tidal turbines or airborne wind energy turbines or in other kinds of turbines dealing with fluid flow whether of gas or of liquid.

The above-described rotor blade configurations may alternatively be employed in aircraft such as commercial airliners, military jet aircraft, helicopter blades, helicopter wings, civilian airplanes, drones, and other similar aircraft. The invention or inventions described herein may be applied to wind turbines having fewer or more blades than described by way of example in order to increase the operational efficiency of a wind turbine, to decrease maintenance costs, and to increase the scalability and marketability of such wind turbines.

A structure as described herein may, as appropriate, contain additional features such as those described in PCT International Patent Application No. PCT/CA2015/050741 to Ryan Church entitled "STRUCTURE WITH RIGID PROJECTIONS ADAPTED TO TRAVERSE A FLUID ENVIRONMENT", and/or those described in PCT International Patent Application No. PCT/CA2015/050740 to Ryan Church entitled "STRUCTURE WITH RIGID WINGLET ADAPTED TO TRAVERSE A FLUID ENVIRONMENT", the contents of each of which are incorporated herein by reference.

Structures such as those described herein may apply equally well, mutatis mutandis, with such mutations as being relevant, including but not limited to, commercial airliners, military jet aircraft, helicopter blades, helicopter wings, civilian airplanes, spacecraft, drones, and other things.

Furthermore, the structures disclosed herein are usable in other fluid environments besides ambient air, such as water environments, oil environments and so forth.

The structure adapted to traverse a fluid environment may be applied to a vertical-axis wind turbine.

The structure adapted to traverse a fluid environment may be applied to a hydroelectric dam turbine.

The structure adapted to traverse a fluid environment may be applied to gas turbines.

The structure adapted to traverse a fluid environment may be applied to tidal turbines.

The structure adapted to traverse a fluid environment may be applied to an airborne wind energy turbine.

The structure adapted to traverse a fluid environment may be applied to a commercial airliner.

The structure adapted to traverse a fluid environment may be applied to a military jet aircraft and to a spacecraft.

The structure adapted to traverse a fluid environment may be applied to a helicopter blade.

The structure adapted to traverse a fluid environment may be applied to helicopter wings.

The structure adapted to traverse a fluid environment may be applied to wings of civilian airplanes.

The structure adapted to traverse a fluid environment may be applied to wings of a drone.

It should be noted that the term 'comprising' does not exclude other elements or steps and the use of articles "a" or "an" does not exclude a plurality. Also, elements described in association with different embodiments may be combined. It should be noted that reference signs in the claims should not be construed as limiting the scope of the claims.

What is claimed is:

1. A wind energy turbine blade component, comprising:
a body having a multi-layer construction having a tip and a root, the body including:
   an interior layer of the body including:
      substantially uniform concentrations throughout of glucose and facultative anaerobic organisms (FAOs) comprising *Saccharomyces cerevisiae* that have gene sets capable of turning glucose into self-assembling nano-fibrils of N-acetylglucosamine to form beta-chitin, and
    - non-uniform concentrations of beta-chitin, beta-chitosan, silk fibronectin and water;
  - an outer-most matrix layer of the body, the outer most matrix layer including urea, water, calcium ions and facultative anaerobic organisms (FAOs) which produce calcium carbonate; and
  - an intermediate layer intermediate the interior layer and the exterior layer of the body, the intermediate layer including conchiolin protein;
- wherein the interior layer of the tip of the body has a differing stiffness compared to the interior layer of the root.

2. The wind energy turbine blade of claim 1, wherein the FAOs further include organisms classified in one of the *Saccharomyces; Escherichia* and *Bacillus* genuses.

3. The wind energy turbine blade of claim 1, the wind energy turbine blade produced by additive manufacturing using multiple layers at least one of which includes both organic and inorganic substances in non-uniform concentrations thereby to provide non-uniform structural properties.

4. The wind energy turbine blade of claim 3, wherein the inner layer, and the outer layer have different compositions, concentrations of underlying materials and pH, relative to each other.

5. The wind energy turbine blade of claim 4, wherein the composition and content of varying FAOs are selected to be adaptable to a particular environment of initial manufacture and the desired material matrix.

6. The wind energy turbine blade of claim 3, wherein the interior layer has substantially uniform concentrations throughout of glucose and FAOs that have gene sets capable of producing the enzyme CHS chitin synthase, and non-uniform concentrations throughout of a structural composition, the structural composition including a chitin-based component with silk fibronectin and water.

7. The wind energy turbine blade of claim 1, wherein the multi-layer construction contains an alternating pattern of layers consisting first of conchiolin, urea, water, calcium ions, amino acids MS160, MSI131 or FAOs that have gene sets capable of producing the enzyme urease or the proteins purloin, lustre A and perlustrin, and consisting second of calcium ions and water.

8. The wind energy turbine blade of claim 4, wherein techniques in synthetic biology are used to produce the FAOs.

9. A wind energy turbine blade of claim 1, where the wind energy turbine blade is printed on-site or in situ, the wind energy turbine blade is produced by multi-material additive manufacturing where:

an additive manufacturing machine with at least one extruder nozzle, at least one actuator motor and an ability to navigate around an entire base and height of the wind energy turbine blade component, the additive manufacturing machine being in fluid communication with a material feedstock(s) adds successive layers of various material to a base; wherein the additive manufacturing machine is configured using processor readable program code stored on a processor-readable medium containing data for the overall shape of the the wind energy turbine blade component and the material concentrations, spacings and gradients.

10. The wind energy turbine blade of claim 9, whereby a deposition speed between the successive layers is based on a speed of self-assembly, a speed of polymerization and linkage speed of the varying elements.

11. The wind energy turbine blade of claim 3, wherein the multiple layers contain uniform concentrations throughout of FAOs, wherein the FAOs are selected to provide gene set availability, environmental message delivery, protein secretion or material production after initial deposition.

12. The wind energy turbine blade of claim 1, wherein the wind energy turbine blade is connected to a vertical wind turbine.

13. The wind energy turbine blade of claim 1, wherein the FAOs of the outer-most matrix layer, as a result of contact with conchiolin protein, produce calcium carbonate in a structural form of layers of beta-pleated sheets of aragonite between alternating conchiolin layers.

14. The wind energy turbine blade of claim 1, wherein the FAOs of the interior layer act in a self-healing matter upon environmental stimulus.

15. The wind energy turbine blade of claim 1, wherein the body further comprises an outer skin including mineral-fibres and chitin in a lattice network with hollow spaces.

16. The wind energy turbine blade of claim 15, wherein the hollow spaces of the lattice network are filled with a gas beneficial to the growth of a single-celled organism.

17. The wind energy turbine blade of claim 1, wherein, in response to being revealed, the interior layer equilibrates to an ambient environmental condition, causing a change in metabolic conditions of the FAOs within the interior layer.

* * * * *